United States Patent [19]

Duffett

[11] Patent Number: Plant 5,777

[45] Date of Patent: Aug. 5, 1986

[54] CHRYSANTHEMUM PLANT NAMED DEEP LUV

[75] Inventor: William E. Duffett, Salinas, Calif.

[73] Assignee: Yoder Brothers, Inc., Barberton, Ohio

[21] Appl. No.: 675,648

[22] Filed: Nov. 28, 1984

[51] Int. Cl.[4] ..... A01H 5/00

[52] U.S. Cl. ..... Plt./76

[58] Field of Search ..... Plt./74, 76

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Deep Luv having flat capitulum form; decorative capitulum type; red purple ray floret color; diameter across face of capitulum ranging from 9 to 11 cm. at maturity; uniform eight week photoperiodic flowering response to short days; short plant height when grown as a pinched, disbud pot mum; and semi-spreading branching pattern.

3 Drawing Figures

The present invention comprises a new and distinct cultivar of *Chrysanthemum morifolium,* Ramat., named Deep Luv.

Deep Luv is a product of a planned sport induction program which had the objective of creating a new chrysanthemum cultivar that would expand the color range of an existing cultivar while retaining all other original traits.

Deep Luv was discovered and selected by William E. Duffett on Aug. 28, 1981 in a controlled environment in Salinas, Calif. as one flowering plant, a color variant within a flowering block established as rooted cuttings from stock plants which had been exposed as unrooted cuttings to an X-ray source of 1000 rads. The irradiated cultivar was True Luv, disclosed in pending application Ser. No. 473.565 and originated by the present inventor.

The first act of asexual reproduction of Deep Luv was accomplished when vegetative cuttings were taken from the initial selection in May 1982 in a controlled environment in Salinas, Calif. by a technician working under formulations established and supervised by William E. Duffett. Horticultural examination of selected units initiated August 1982 has demonstrated that the combination of characteristics as herein disclosed for Deep Luv are firmly fixed and are retained through successive generations of asexual reproduction.

Deep Luv has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Deep Luv which in combination distinguish this chrysanthemum as a new and distinct cultivar:

(1) Flat capitulum form.

(2) Decorative capitulum type.

(3) Red purple ray floret color.

(4) Diameter across face of capitulum ranging from 9 to 11 cm. at maturity.

(5) Uniform eight week photoperiodic flowering response to short days.

(6) Short plant height, requiring 2 long day weeks prior to pinch followed by 3 to 7 long days prior to short days, and 0 to 1 application of 2500 ppm B-9 SP in 7 to 14 days after the beginning of short days to attain a flowered plant height of 25 to 35 cm. in 6″ pots.

(7) Semi-spreading branching pattern.

The accompanying photographic drawings depict typical foliage and inflorescence characteristics of Deep Luv. Sheet 1 is a color photograph of a plant of Deep Luv grown as a pinched, disbud pot mum, with colors being as accurate as possible with renditions of this type. Sheet 2 is a black and white photograph of three views of the inflorescence of Deep Luv. Sheet 3 shows the upper surface of the leaves of Deep Luv in three stages of development (mature, intermediate and immature).

Of the many commercial cultivars known to the present inventor the most similar in comparison to Deep Luv is the parent cultivar True Luv. Reference is made to attached Chart A which compares certain characteristics of Deep Luv to those same characteristics of True Luv.

Deep Luv is very similar to True Luv in all respects except color. The color of Deep Luv is significantly darker than that of True Luv, and has superior color retention due to a slower rate of color oxidation. The undesirable fading of the floret tips characteristic of True Luv is corrected to a high degree by Deep Luv.

In the following description, color references are made to The Royal Horticultural Society Colour Chart. The color values were determined between 9:00 and 9:15 a.m. on June 19, 1984 under 380 foot-candle light intensity at Salinas, Calif.

Classification

*Botanical.*—*Chrysanthemum morifolium,* Ramat., cv Deep Luv

*Commercial.*—Decorative disbud pot mum.

I. Inflorescence:

A. *Capitulum.*—Form: Flat. Type: Decorative. Diameter Across Face: 9 to 11 cm.

B. *Corolla of ray florets.*—Color (General Tonality From a Distance of Three Meters): Red purple. Color (upper surface): 71C–71D. Color (under surface): 75A, 75B. Shape: Oblong, rounded tip, sometimes notched.

C. *Corolla of disc florets.*—Color (mature): 154A. Color (immature): 145A.

D. *Reproductive organs.*—Androecium: Present disc florets only; very few; scant pollen. Gynoecium: Present both ray and disc florets.

II. Plant:

A. *General appearance.*—Height: Short; 25 to 35 cm. in 6" pots given 2 long day weeks prior to pinch plus 3–7 long days prior to short days and 0–1 application of 2500 ppm B-9 SP. Branching Pattern: Semi-spreading.

B. *Foliage.*—Color (upper surface): 147A. Color (under surface): 147B. Shape: Deeply lobed. Moderately serrated.

CHART A

COMPARISON OF DEEP LUV AND TRUE LUV

| CULTIVAR | RAY FLORET COLOR | CAPITULUM FORM AND TYPE |
|---|---|---|
| DEEP LUV | RED PURPLE | FLAT DECORATIVE |
| TRUE LUV | DEEP LAVENDER | FLAT DECORATIVE |

| CULTIVAR | BRANCHING PATTERN | DIAMETER ACROSS FACE OF CAPITULUM |
|---|---|---|
| DEEP LUV | SEMI- | 9 to 11 cm. |

CHART A-continued

COMPARISON OF DEEP LUV AND TRUE LUV

| | | |
|---|---|---|
| TRUE LUV | SPREADING SEMI-SPREADING | 10.5 to 11.5 cm. |

| CULTIVAR | PLANT HEIGHT | FLOWERING RESPONSE PERIOD |
|---|---|---|
| DEEP LUV | SHORT 25 to 35 cm. | 8 WEEKS |
| TRUE LUV | SHORT 25 to 35 cm. | 8 WEEKS |

COMPARISONS MADE OF PLANTS GROWN AS PINCHED DISBUD POT MUMS IN SALINAS, CALIFORNIA AND LEAMINGTON, ONTARIO, CANADA

I claim:

1. A new and distinct cultivar of *Chrysanthemum morifolium,* Ramat., plant named Deep Luv, as described and illustrated, and particularly characterized as to uniqueness by the combined characteristics of flat capitulum form; decorative capitulum type; red purple ray floret color; diameter across face of capitulum ranging from 9 to 11 cm. at maturity; uniform eight week flowering response; short plant height, and semi-spreading branching pattern.

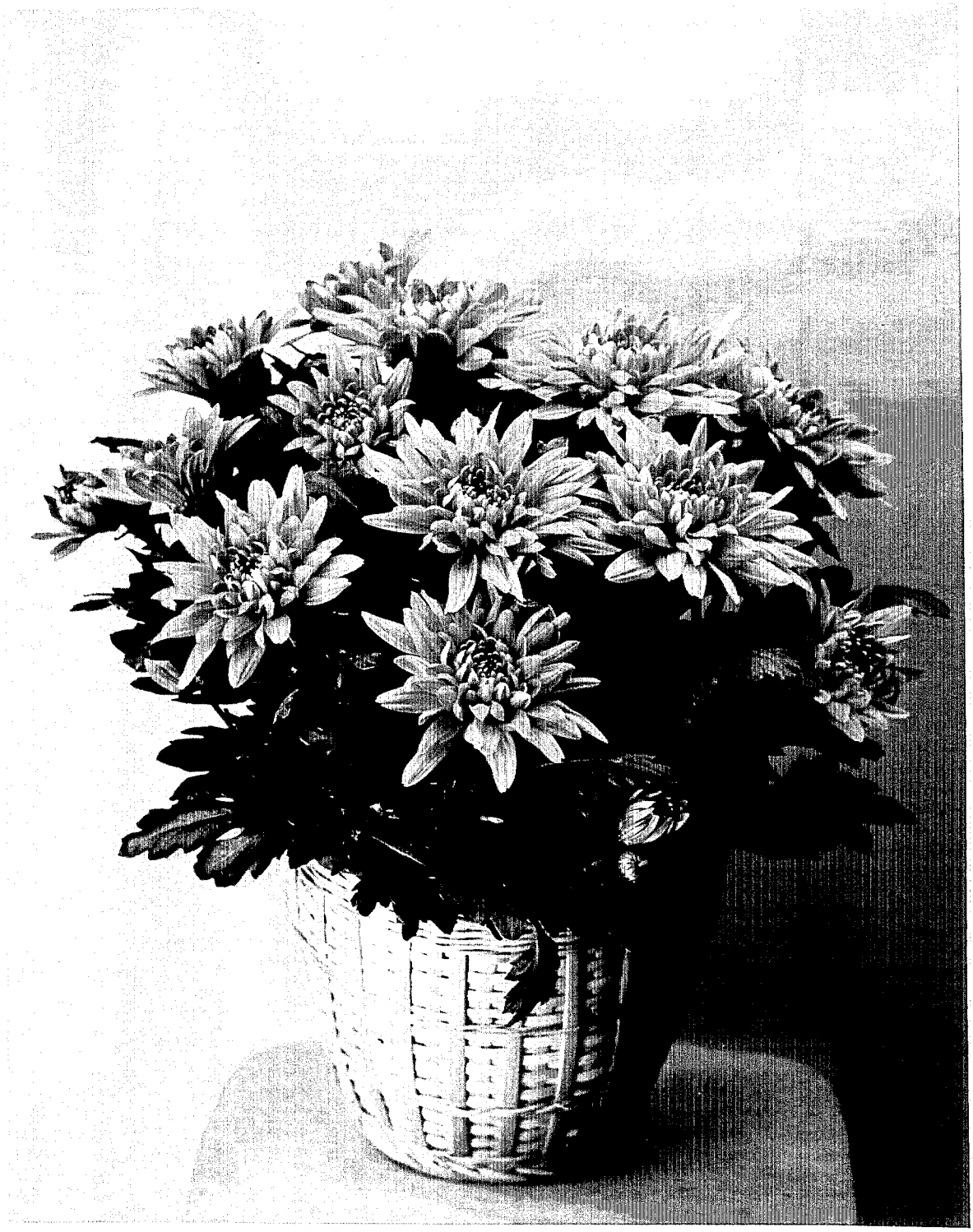

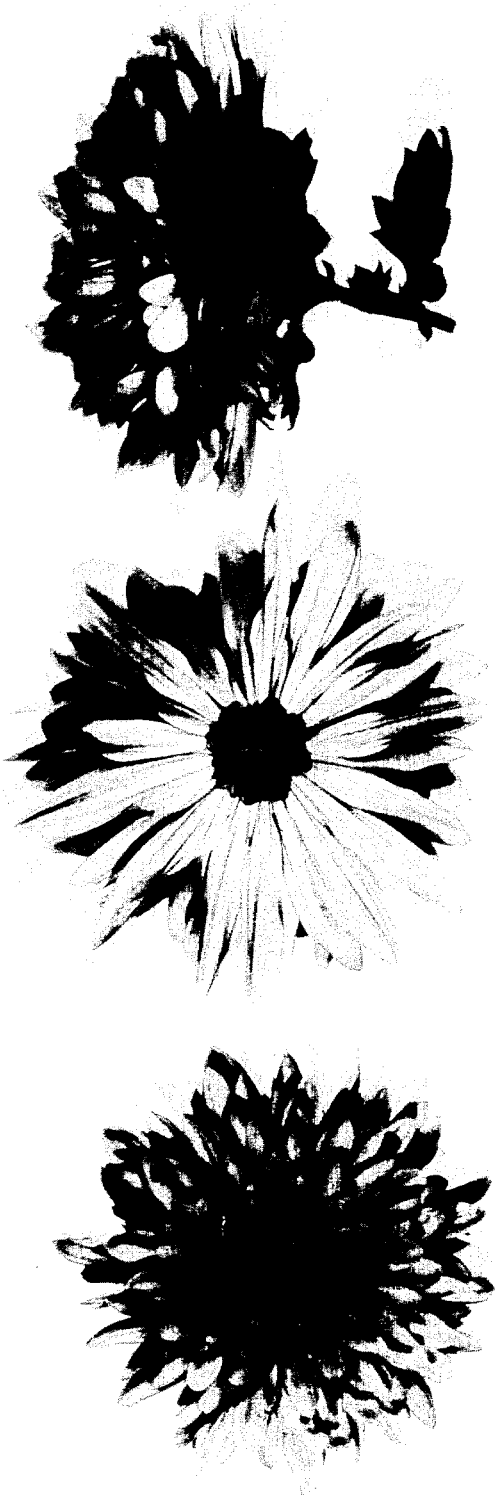

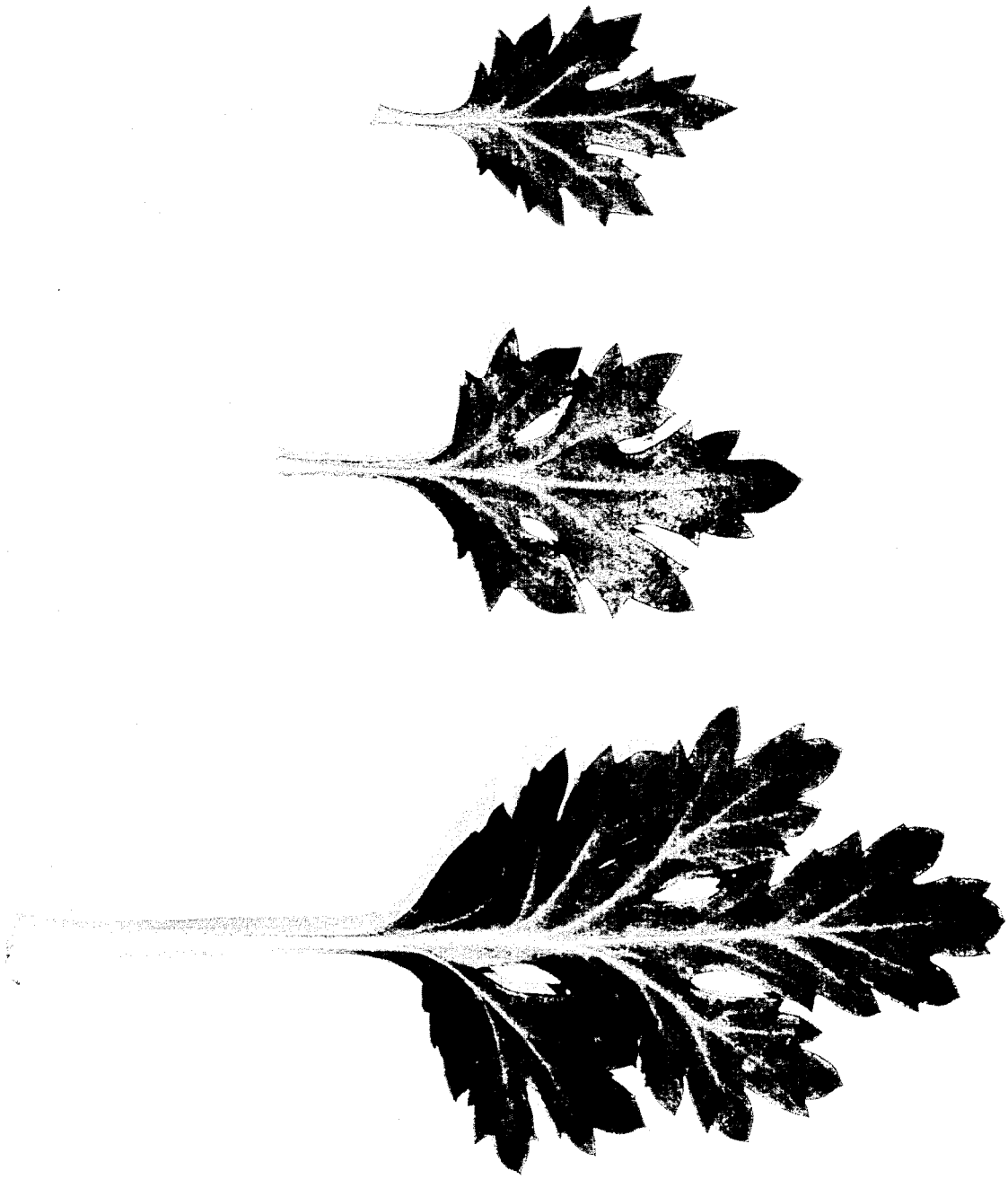

* * * * *